United States Patent [19]
Suzuki et al.

[11] Patent Number: 5,763,333
[45] Date of Patent: Jun. 9, 1998

[54] COMPOSITE SHEET, ABSORBENT ARTICLE AND PROCESS FOR PRODUCING THE SAME

[75] Inventors: Mikio Suzuki; Katsushi Maeda; Masao Kurahashi; Kazuo Fujita, all of Haga-gun, Japan

[73] Assignee: Kao Corporation, Tokyo, Japan

[21] Appl. No.: 820,042

[22] Filed: Mar. 19, 1997

[30] Foreign Application Priority Data

Mar. 19, 1996 [JP] Japan .................................. 8-063055

[51] Int. Cl.⁶ .................................................. B32B 7/00
[52] U.S. Cl. ...................... 442/351; 442/340; 442/394; 442/398; 428/332; 428/340; 156/334
[58] Field of Search ........................ 428/332, 340; 442/340, 351, 394, 398; 156/334

[56] References Cited

U.S. PATENT DOCUMENTS

| | | |
|---|---|---|
| 4,886,853 | 12/1989 | Foster et al. .................... 524/477 |
| 4,939,202 | 7/1990 | Maletsky et al. ................. 524/528 |
| 4,998,928 | 3/1991 | Maletsky et al. ................. 604/365 |
| 5,021,257 | 6/1991 | Foster et al. .................... 427/2 |

FOREIGN PATENT DOCUMENTS

WO8905334  6/1989  WIPO.

*Primary Examiner*—Christopher Raimund
*Attorney, Agent, or Firm*—Birch, Stewart, Kolasch & Birch, LLP

[57] ABSTRACT

A composite sheet comprising a liquid impermeable sheet and a nonwoven fabric joined to each other by an adhesive composition, the liquid impermeable sheet having a thickness of 15 to 40 μm; the nonwoven fabric having a fiber diameter of 1.5 to 3.5 deniers and a basis weight of 10 to 35 g/m²; and the adhesive composition comprising not less than 20% by weight of an amorphous poly-α-olefin (APAO) having a melt viscosity of 500 to 10,000 cps at 180° C. and applied at an amount of 0.5 to 7 g/m².

10 Claims, 1 Drawing Sheet

COMPOSITE SHEET, ABSORBENT ARTICLE AND PROCESS FOR PRODUCING THE SAME

FIELD OF THE INVENTION

The present invention relates to a composite sheet suitable for use as a back sheet of absorbent articles, such as disposable diapers. The present invention also relates to an absorbent article using the composite sheet and to a process for producing the absorbent article.

BACKGROUND OF THE INVENTION

In the field of absorbent articles, such as disposable diapers, a composite sheet comprising of a moisture permeable sheet and a nonwoven fabric laminated to each other by a rubber-type hot melt adhesive predominantly comprising SIS (styrene-isoprene-styrene), SBS (styrene-butadiene-styrene) or a mixture thereof is used as an outermost back sheet in order to secure breathability (good ventilation) and to improve texture or feel.

Such a composite sheet is generally stored in a rolled form, which is unrolled upon use for the manufacture of, for instance, disposable diapers. Where thin and open weave nonwoven fabric is used in the composite sheet from consideration of texture or feel, the adhesive would unfavorably bleed (migrate) out onto the surface of the nonwoven fabric under the pressure of the roller and stick to the adjacent layer of the sheet (This phenomenon is called blocking). The rolled composite sheet having undergone blocking will be broken or cling to the roller when it is unrolled.

If the amount of the adhesive is decreased so as to avoid blocking, the adhesive strength between the moisture permeable sheet and the nonwoven fabric will be insufficient for use as a back sheet for absorbent articles such as disposable diapers.

SUMMARY OF THE INVENTION

Accordingly, an object of the present invention is to provide a composite sheet which has high adhesive strength and prevents blocking.

Another object of the invention is to provide an absorbent article having breathability and an improved texture or touch, such as improved softness.

A further object of the invention is to provide a process for producing an absorbent article using a composite sheet as a back sheet, in which the composite sheet has high adhesive strength and is free from troubles due to blocking when the rolled composite sheet is unrolled.

As a result of extensive investigation, the inventors of the present invention have found that the above objects of the present invention can be accomplished by a composite sheet comprising a sheet having specific physical properties and a nonwoven fabric having specific physical properties joined to each other by an adhesive composition having specific physical properties. The present invention has been completed based on these findings.

The present invention provides a composite sheet comprising a liquid impermeable sheet and a nonwoven fabric joined to each other by an adhesive composition, said liquid impermeable sheet having a thickness of 15 to 40 µm; the nonwoven fabric having a fiber diameter of 1.5 to 3.5 deniers and a basis weight of 10 to 35 g/m$^2$; and the adhesive composition comprising not less than 20% by weight of an amorphous poly-α-olefin (APAO) having a melt viscosity of 500 to 10,000 cps at 180° C. and applied at an amount of 0.5 to 7 g/m$^2$.

The present invention further provides an absorbent article comprising a liquid permeable topsheet, a liquid impermeable back sheet and an absorbent member interposed between the topsheet and the back sheet, wherein the back sheet comprises the above-mentioned composite sheet.

The present invention further provides a process for producing an absorbent article having a liquid impermeable back sheet which is a composite sheet comprising a liquid impermeable sheet and a nonwoven fabric joined to each other by an adhesive composition, said liquid impermeable sheet having a thickness of 15 to 40 µm; the nonwoven fabric having a fiber diameter of 1.5 to 3.5 deniers and a basis weight of 10 to 35 g/m$^2$; and the adhesive composition comprising not less than 20% by weight of an amorphous poly-α-olefin (APAO) having a melt viscosity of 500 to 10,000 cps at 180° C. and applied at an amount of 0.5 to 7 g/m$^2$, the process comprising the steps of applying the adhesive composition on the liquid impermeable sheet, laminating the nonwoven fabric to the liquid impermeable sheet via the adhesive composition, and securely joining the liquid impermeable sheet and the nonwoven fabric to each other by joining means.

The present invention further provides a process for producing a composite sheet comprising a liquid impermeable sheet and a nonwoven fabric joined to each other by an adhesive composition, said liquid impermeable sheet having a thickness of 15 to 40 µm; the nonwoven fabric having a fiber diameter of 1.5 to 3.5 deniers and a basis weight of 10 to 35 g/m$^2$; and the adhesive composition comprising not less than 20% by weight of an amorphous poly-α-olefin (APAO) having a melt viscosity of 500 to 10,000 cps at 180° C. and applied at an amount of 0.5 to 7 g/m$^2$, the process comprising the steps of applying the adhesive composition on the liquid impermeable sheet, laminating the nonwoven fabric to the liquid impermeable sheet via the adhesive composition, and securely joining the liquid impermeable sheet and the nonwoven fabric to each other by suitable joining means.

According to the present invention, a composite sheet which has high adhesive strength and yet prevents blocking can be obtained. Accordingly, when the composite sheet of the present invention is used in a rolled form in the manufacture of absorbent articles such as a disposable diaper, the composite sheet is effectively prevented from being broken or prevented from clinging to the roller while being unrolled.

Further, the absorbent article of the present invention exhibits breathability and an improved texture or touch, such as improved softness.

Further, according to the process for producing an absorbent article of the present invention, troubles in unrolling the composite sheet, which would be caused by blocking, are effectively avoided.

DETAILED DESCRIPTION OF THE INVENTION

Figure 1:
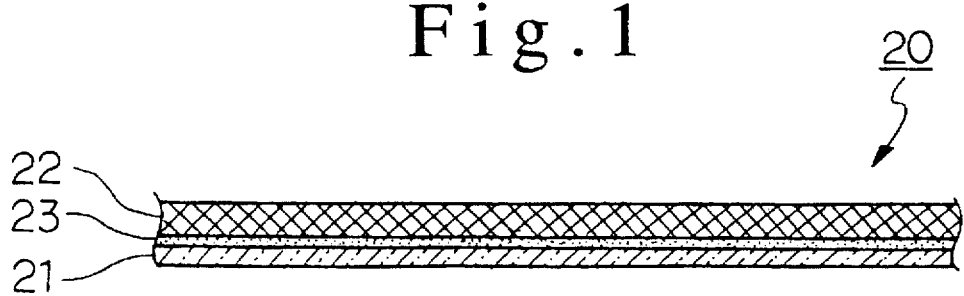
FIG. 1 is a schematic cross section showing a preferred embodiment of the composite sheet according to the present invention.

A preferred embodiment of the composite sheet according to the present invention is described by referring to the accompanying drawing. FIG. 1 is a schematic cross section of a preferred embodiment of the composite sheet according to the present invention.

A composite sheet 20 shown in FIG. 1 comprises a sheet 21 and a nonwoven fabric 22 joined (laminated) to each other by an adhesive composition 23. The sheet 21, the nonwoven fabric 22 and the adhesive composition 23 used in the composite sheet 20 have the following physical properties.

The sheet 21 comprises a liquid impermeable sheet having a thickness of 15 to 40 μm.

The nonwoven fabric 22 has a fiber diameter of 1.5 to 3.5 deniers and a basis weight of 15 to 35 g/m².

The adhesive composition 23 comprises not less than 20% by weight of an amorphous poly-α-olefin (hereinafter referred to as APAO) having a melt viscosity of 500 to 10,000 cps at 180° C. and is applied at an amount of 0.5 to 7 g/m².

(1) The sheet 21, (2) the nonwoven fabric 22, and (3) the adhesive composition 23 will further be described below.

(1) Sheet:

A liquid impermeable film sheet having the above specified thickness is suitably used as sheet 21. The sheet 21 may be either moisture permeable or impermeable. A moisture permeable sheet is suitable for use as a back sheet of a disposable diaper as hereinafter described because of its expiration of water vapor, providing good ventilation and protection of the wearer from a diaper rash.

The moisture permeable sheet and moisture impermeable sheet will be further described herein below.

(1-1). Moisture Permeable Sheet:

A moisture permeable sheet suitable for use as sheet 21 preferably has a moisture permeability of 0.5 to 4 g/(100 cm².hr), particularly 1.0 to 2.5 g/(100 cm².hr). If the sheet whose moisture permeability is less than 0.5 g/(100 cm².hr) is used as a back sheet of such an absorbent article as a disposable diaper as hereinafter described, breathability is insufficient and a diaper rash cannot be prevented sufficiently. If the moisture permeability exceeds 4 g/(100 cm².hr), there is a fear that liquid (urine, etc.) might leak. The quantitative term "moisture permeability" as used herein is a value measured in accordance with JIS Z 0208.

As described above, the moisture permeable sheet has a thickness of 15 to 40 μm, preferably 20 to 35 μm. If the thickness is less than 15 μm, thickness control of the moisture permeable sheet in the course of its production sometimes becomes difficult, and the sheet tends to break when it is laminated to the nonwoven fabric 22 or when the resulting composite sheet is used in the manufacture of an absorbent article, such as a disposable diaper. If the thickness exceeds 40 μm, the texture or touch, such as softness, of the composite sheet 20 tends to be unfavorably reduced.

The basis weight of the moisture permeable sheet is not particularly limited but is preferably 15 to 40 g/m², still preferably 20 to 35 g/m², from the standpoint of thickness control in the course of production, or texture and touch.

The moisture permeable sheet is preferably a porous sheet having a large number of micropores. Such a porous sheet can be obtained by compounding a polyolefin resin with a filler, melt molding the compound into a film or a sheet, and stretching the resulting film or sheet monoaxially or biaxially by methods well known in the art.

The polyolefin resins include those comprising predominantly a homo- or copolymer of an olefin, e.g., ethylene, propylene or butene. Examples of suitable polyolefin resins are high-density polyethylene, low-density polyethylene, linear low-density polyethylene, polypropylene, a crystalline ethylene-propylene block copolymer, polybutene, an ethylene-vinyl acetate copolymer, and a mixture thereof. Linear low-density polyethylene is particularly preferred for its suppleness and toughness.

The fillers include organic or inorganic fillers. Suitable inorganic fillers include calcium carbonate, gypsum, talc, carbon black, clay, kaolin, silica, diatomaceous earth, magnesium carbonate, barium carbonate, magnesium sulfate, barium sulfate, calcium sulfate, calcium phosphate, aluminum hydroxide, zinc oxide, magnesium hydroxide, calcium oxide, magnesium oxide, titanium oxide, alumina, mica, asbestos powder, sirasu balloon, zeolite, terra alba, cement, silica fume, and mica powder. Usable organic fillers include woodmeal, coal powder, and pulp powder. These fillers can be used either individually or as a mixture thereof The filler preferably has an average particle size of not greater than 30 μm, particularly not greater than 10 μm, especially from 0.5 to 5 μm. From the viewpoint of uniform dispersibility in the polyolefin resin matrix, the filler is preferably subjected to surface treatment. The surface treatment is preferably carried out with a substance capable of rendering the surface of the fillers hydrophobic, such as fatty acids and their metal salts. The filler is preferably used in an amount of 50 to 250 parts by weight per 100 parts by weight of the polyolefin resin.

The polyolefin resin may contain various other components for improving various properties of the microporous sheet.

For example, for the purpose of improving the tear strength in the stretch direction and the tensile stress in the lateral direction, the polyolefin resin may contain an olefinic low-melting polymer, a liquid or waxy hydrocarbon polymer, a rubbery compound (e.g., natural rubber, isoprene rubber, butadiene rubber, etc.), an olefinic thermoplastic elastomer, a styrene-based thermoplastic elastomer, and a plasticizer.

For the purpose of improving the sheet strength and of forming continuous pores even at a low stretch ratio, 1 to 100 parts by weight of a triglyceride can be added to 100 parts by weight of the polyolefin. Preferred fatty acids providing the triglyceride are saturated or unsaturated fatty acids having 2 to 30 carbon atoms.

For the same purpose of improving the sheet strength, chlorinated paraffin may be used. In this case, chlorinated paraffin having a chlorine content of 1 to 65% by weight, particularly 35 to 55% by weight, is preferably used. Such chlorinated paraffin is prepared by a known method, for example, by bubbling chlorine gas through a carbon tetrachloride solution of molten solid paraffin, n-paraffin or solid paraffin. The chlorinated paraffin is preferably used, if added, in an amount of 1 to 100 parts by weight per 100 parts by weight of the polyolefin resin.

For this same purpose, a mixture of a monoester comprising a monobasic acid and a monohydric alcohol and a polyester comprising a polybasic acid and a polyhydric alcohol can be also used. The monoesters include those prepared by carrying out the dehydration condensation of a monobasic acid, such as a monocarboxylic acid having 10 or more carbon atoms, and a monohydric alcohol, such as a monoalcohol having 10 or more carbon atoms. Monoesters having a molecular weight of more than 240, particularly those having 20 or more carbon atoms and containing a branched hydrocarbon chain, are preferred. On the other hand, the polyesters include those obtained by carrying out the dehydration condensation of a polybasic acid, such as a dicarboxylic acid, a tricarboxylic acid or a tetracarboxylic acid, and a polyhydric alcohol, such as diols, trimethylolpropane, pentaerythritol, dipentaerythritol, sorbitol or sucrose, and having 50 or more carbon atoms in total. The monoester/polyester mixture is preferably used, if added, in an amount of 5 to 50 parts by weight per 100 parts by weight of the polyolefin resin. It is considered that the monoester contributes to improvement on the moisture permeability and longitudinal tear strength, while the polyester contributes to improvement on the moisture permeability and outer appearance.

For this same purpose, a mixture of polyester A comprising a polybasic acid and a monohydric alcohol and polyester B comprising a polybasic acid and a polyhydric alcohol can also be used. The polyesters A can be a di-, tri- or tetraester obtained by carrying out the dehydration condensation of a polybasic acid, such as a di-, tri- or tetracarboxylic acid, and a monohydric alcohol and having 30 or more carbon atoms in total. Preferred of them are diesters having a saponification value of 230 or lower. Diesters containing a branched monohydric alcohol having 16 or more carbon atoms are still preferred. The polyesters B include those obtained by carrying out the dehydration condensation of a polybasic acid, such as a di-, tri- or tetracarboxylic acid, and a polyhydric alcohol, such as a diol, trimethylolpropane, pentaerythritol, dipentaerythritol, sorbitol or sucrose, and having 50 or more carbon atoms in total. The polyester A/polyester B mixture is preferably used, if added, in an amount of 5 to 50 parts by weight per 100 parts by weight of the polyolefin resin.

For the purpose of improving longitudinal tear strength while retaining a supple texture, satisfactory moisture permeability and leakproofness, a monoester having 38 or more carbon atoms in which either one or both of the acid and alcohol components has/have a branched structure can be used. Examples of such a monoester include 2-decyltetradecyl stearate, 2-octadecyl behenate, and an ester of an α-branched fatty acid having 18 to 40 carbon atoms and a monoalcohol having 6 to 36 carbon atoms (having 38 or more carbon atoms in total). The monoester is preferably used, if added, in an amount of 5 to 50 parts by weight per 100 parts by weight of the polyolefin resin.

For this same purpose as described above and also for the purpose of improving the appearance of the sheet, a mixture of a hydrocarbon polymer having a side chain and a polyester can be used. The hydrocarbon polymer having a side chain can be preferably an α-olefin oligomer having a side chain containing 4 or more carbon atoms. In addition, an ethylene-propylene copolymer, e.g., LUCANT (a trade name, produced by Mitsui Petrochemical Industries, Ltd.) or a maleic acid derivative thereof, an isobutylene polymer, e.g., Polybutene HV-100 (a trade name, produced by Idemitsu Petrochemical Co., Ltd.), a butadiene or isoprene oligomer or a hydrogenation product thereof, and derivatives derived from these compounds can be also used. The polyester to be mixed with can be, for example, a polyester comprising a polybasic acid or a polyhydric alcohol. Preferred polyesters include castor oil, hydrogenated castor oil, an ethylene oxide adduct of hydrogenated castor oil, a polyester prepared from a glycol and a dimeric acid, a hexaester prepared from trimethylolpropane, a dimeric acid and stearic acid, and a hexaester prepared from trimethylolpropane, adipic acid and stearic acid. The mixing ratio of the hydrocarbon polymer having a side chain and the polyester is arbitrarily selected from the range 1/9 to 9/1 by weight depending on desired levels of moisture permeability, longitudinal tear strength and appearance according to the end use and is preferably from 3/7 to 7/3 by weight. The hydrocarbon polymer/polyester mixture is preferably used, if added, in an amount of 5 to 50 parts by weight per 100 parts by weight of the polyolefin resin.

The moisture permeable microporous sheet suitable for use in the present invention can also be a microporous sheet obtained by forming a sheet comprising a mixture of (a) a crystalline polyolefin resin and (b) an organic compound that is miscible with the melt of the crystalline polyolefin (a) but forms a separate phase at a temperature below the crystallization temperature of the crystalline polyolefin resin (a), and stretching the resulting sheet at least monoaxially.

The crystalline polyolefin resin (a) preferably includes polypropylene, a blend of polypropylene and a propylene-ethylene copolymer, and a blend of polypropylene and polyethylene.

The organic compound (b) preferably includes a mineral oil, a synthetic lubricating oil, paraffin wax, and an ester of an aliphatic carboxylic acid and a polyhydric alcohol.

The crystalline polyolefin resin (a) and the organic compound (b) are preferably used in an amount of 50 to 90 parts by weight and 10 to 50 parts by weight, respectively.

It is preferable to incorporate various additives, such as a nucleating agent, into the above-described porous sheet. Such an additive is preferably added in an amount of 0.01 to 3 parts by weight, particularly 0.05 to 1 part by weight, per 100 parts by weight of the mixture of the crystalline polyolefin resin (a) and the organic compound (b).

A preferred stretch ratio in stretching the sheet prepared from the mixture of the crystalline polyolefin resin (a) and the organic compound (b) is at least monoaxially 1.2 to 5, particularly 1.2 to 3, in terms of area ratio.

(1-2) Moisture Impermeable Sheet:

The moisture impermeable sheet suitable for use as sheet 21 will now be described. With respect to the moisture impermeable sheet, particulars different from the above-described moisture permeable sheet will be described, and as regards the other points, the foregoing description on the moisture permeable sheet applies.

The moisture impermeable sheet can be a general moisture impermeable and liquid impermeable sheet which is obtained by blending a mixture comprising, as a major component, a polyolefin resin and additives such as a pigment and a filler, forming a sheet from the mixture by means of a T-die extruder or a blown-film extruder. A polyethylene resin-based sheet is preferred as the moisture impermeable sheet. The basis weight of the moisture impermeable sheet is preferably 10 to 50 g/m².

(2) Nonwoven Fabric:

As described above, fibers constituting the nonwoven fabric 22 have a diameter of 1.5 to 3.5 deniers, preferably 1.5 to 3.0 deniers, still preferably 1.5 to 2.0 deniers. If the fiber diameter is less than 1.5 deniers, it is difficult to produce the nonwoven fabric 22 and it becomes costly to produce thereof although the texture or touch (e.g., softness) of the nonwoven fabric 22 becomes satisfactory. If the fiber diameter is more than 3.5 deniers, the nonwoven fabric 22 has deteriorated texture or touch (e.g., softness).

The fibers constituting the nonwoven fabric 22 are not particularly limited in form or material as far as the fiber diameter falls within the above range. Either long continuous filaments or staple fibers may be used. The fibers include thermoplastic synthetic fibers, such as polyethylene fibers, polypropylene fibers, polyester fibers and polyamide fibers;

natural fibers, such as cotton, hemp and wool; and regenerated fibers, such as rayon fibers and acetate fibers.

As described above, the nonwoven fabric 22 has a basis weight of 10 to 35 g/m², preferably 15 to 35 g/m², still preferably 18 to 25 g/m². If the basis weight is less than 10 g/m², the nonwoven fabric 22 has the following disadvantages: (1) the strength is reduced; (2) the uniform formation of the nonwoven fabric 22 is deteriorated to cause conspicuous blocking; and (3) the productivity decreases although the texture or touch (e.g., softness) of the nonwoven fabric 22 becomes satisfactory. If the basis weight is higher than 35 g/m², the texture or touch (e.g., softness) of the nonwoven fabric 22 is deteriorated.

The nonwoven fabric 22 is not limited in process of production. For example, nonwoven fabric manufactured by known processes, such as suction heat bonding using a carding machine, spun bonding, melt blowing, spun lacing, and needle punching, can be used.

While the thickness of the nonwoven fabric 22 is not limited, it is preferably 0.1 to 2 mm, particularly 0.3 to 1.0 mm, under a load of 0.5 g/cm² from the viewpoint of texture or touch (e.g., softness), prevention of blocking caused by non-uniform formation of the nonwoven fabric 22, and productivity.

(3) Adhesive Composition:

As described above, the adhesive composition 23 comprises not less than 20% by weight, preferably 30 to 100% by weight of an amorphous poly-α-olefin (APAO). An adhesive composition containing 20% by weight or more of APAO has favorable flowability, resulting in excellent impregnation among the fibers of the nonwoven fabric 22 upon application and, after setting, becomes hardly flowable at room temperature, resulting in reduced tack (stickiness). As a result, high adhesive strength can be obtained between the sheet 21 and the nonwoven fabric 22, and blocking is effectively prevented.

APAO is used as a base polymer of the adhesive compositon. Any known kind of APAO can be used without particular limitation. Examples of APAO are a propylene-ethylene copolymer, a propylene-butene-1 copolymer, and a propylene-hexene copolymer. These APAO polymers are commercially available under the trade name "Ubetack" produced by Ube Rexene K. K., and "East Flex" produced by Eastman Kodak Co., Ltd.

A propylene-ethylene-butene-1 terpolymer can also be used as APAO, which is commercially available from Hultz under the trade name "Best Plast".

The adhesive composition 23 may comprise 100% of APAO, or alternatively may further contain one or more of a tackifier, a softener and an antioxidant.

The tackifiers that are solid at room temperature are preferred for use. Such tackifiers include a C5-based petroleum resin, a C9-based petroleum resin, a dicyclopentadiene-based petroleum resin, a rosin-based petroleum resin, a polyterpene resin, and a terpene phenol resin. Specific examples include hydrogenated terpene resins, such as "Clearon" (a trade name of Yasuhara Kagaku K. K.), and hydrogenated aromatic petroleum resins, such as "Alcon" (a trade name of Arakawa Kagaku K. K.). The tackifier can be used in an amount selected appropriately according to the amount of the softener used in combination, usually ranging from 30 to 70% by weight based on the total weight of the adhesive compostion.

The softeners preferred for use include mineral oil, various plasticizers, polybutene, liquid tackifying resins and process oil having a softening point of 10° C. or below and an average molecular weight of 200 to 700. Specific examples include paraffin oils, such as "Shell Flex" (a trade name of Shell Chemical Co., Ltd.) and "PW-90" (a trade name of Idemitsu Kosan K. K.); and ester oils, such as tetraoctyl pyromellitate, di-dodecyl phthalate, and trioctyl trimellitate. The softener is preferably used in an amount of not more than 20% by weight based on the total weight of the adhesive composition. If the amount of the softener exceeds 20% by weight, the adhesive composition becomes tacky or sticky, tending to cause blocking between adjacent layers of the composite sheet 20.

The antioxidant preferably includes "Irganox 1010" (a trade name of Ciba-Geigy Ltd.), "Irganox 1076" (a trade name of Ciba-Geigy Ltd.), and "Sumilizer GM" (a trade name of Sumitomo Chemical Co., Ltd.). The antioxidant is preferably used in an amount of 1 to 3 parts by weight per 100 parts by weight of APAO.

If desired, the adhesive composition 23 may contain other components in addition to the above-mentioned components.

As described above, the adhesive composition 23 has a melt viscosity of from 500 to 10,000 cps, preferably 1,000 to 8,000 cps, still preferably 1,000 to 6,000 cps, at 180° C. If the melt viscosity is less than 500 cps, unfavorable non-uniform coating of the adhesive composition 23 in the width direction or drops of the adhesive composition 23 upon coating may be occurred. If the melt viscosity exceeds 10,000 cps, the applicability of the adhesive composition 23 is reduced, causing the occurrence of unfavorable non-uniform coating or drops of the adhesive composition 23 upon coating.

As described above, the adhesive composition 23 is applied at an amount of 0.5 to 7 g/m², preferably 0.5 to 5 g/m², still preferably 0.5 to 3 g/m². If the amount is less than 0.5 g/m², sufficient adhesive strength cannot be secured between the sheet 21 and the nonwoven fabric 22. If the spread exceeds 5 g/m², the texture of the composite sheet 20 is reduced, and blocking occurs between the adjacent layers of the composite sheet 20 although the sufficient adhesive strength can be secured.

The adhesive composition 23 may be applied to the entire interface between the sheet 21 and the nonwoven fabric 22. However, in view of the texture, or maintaining the sufficient moisture permeability in case the sheet 21 comprises a moisture permeable sheet, the adhesive composition 23 is preferably applied discontinuously, for example, in lines, dots, squares or spiral patterns. In the latter case where the adhesive composition 23 is applied discontinuously, it is preferable to apply the adhesive composition to provide an adhesive area ratio of 20 to 60% with the amount of the adhesive composition falling within the above range.

Known methods for applying the adhesive composition 23 include slot spraying in which the adhesive composition is atomized and applied in dots, curtain spraying, melt blowing, spiral spraying, gravure coating, and application in lines.

After the sheet 21 and the nonwoven fabric 22 are laminated by the adhesive composition, it is preferred that the sheet 21 and the nonwoven fabric 22 of the resulting composite sheet 20 shown in FIG. 1 is securely joined to each other by joining means such as heat embossing and heat rollering, in particular heat embossing. That is, the composite sheet 20 is preferably prepared by laminating the sheet 21 and the nonwoven fabric 22 to each other by the adhesive composition 23 and securely joining them by heat embossing. Heat embossing not only makes the adhesive strength between the sheet 21 and the nonwoven fabric 22 stronger but is effective in improving the texture, softness and touch of the composite sheet 20. Heat embossing is also effective in preventing wrinkles on shrinkage that would be caused by the difference between the sheet 21 and the nonwoven fabric 22 in tension (or elongation) in the course of lamination therebetween.

The heat embossing of the composite sheet 20 is preferably carried out to an embossed area ratio of not more than 40%, particularly 10 to 30%, based on the total area of the composite sheet. If the embossed area ratio exceeds 40%, the composite sheet 20 becomes too hard to have a satisfactory texture or touch (e.g., softness) or to retain desired moisture permeability.

The details of the heat embossing, such as conditions, will be described hereinbelow.

In the composite sheet 20 shown in FIG. 1, since the sheet 21 and the nonwoven fabric 22 are laminated by the above-described adhesive composition, the composite sheet 20 exhibits high adhesive strength between the sheet 21 and the nonwoven fabric 22 and effectively prevents blocking. More specifically, the adhesive strength between the sheet 21 and the nonwoven fabric 22 is preferably 30 g/25 mm or higher, particularly 50 g/25 mm or higher, especially 100 g/25mm or higher. There is no particular upper limit of the adhesive strength (the higher, the better).

The anti-blocking strength of the composite sheet is preferably 20 g/50 mm or less, particularly 15 g/50 mm or less, especially 10 g/50 mm or less. There is no particular lower limit of the anti-blocking strength (the lower, the better).

The methods for measuring the adhesive strength and the anti-blocking strength will be explained in the Examples hereinafter given.

Figure 2:
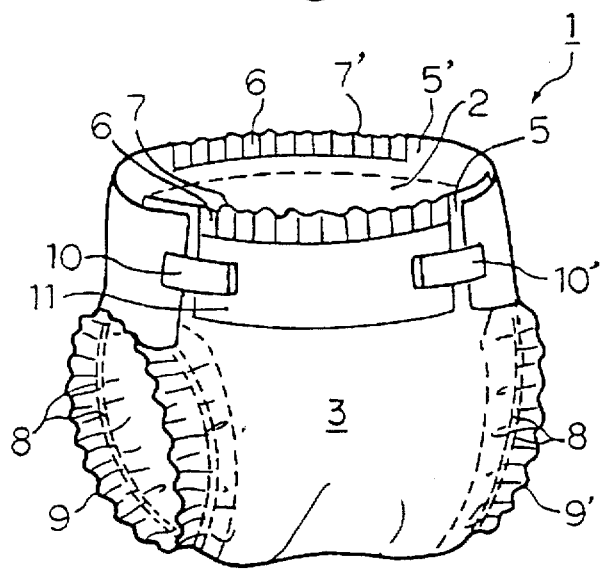
FIG. 2 is a perspective view of a disposable diaper as a preferred embodiment of the absorbent article according to the present invention.

A preferred embodiment of the absorbent article according to the present invention which uses the composite sheet 21 of FIG. 1 is now described by referring to FIG. 2. In FIG. 2 is shown a perspective view of a disposable diaper as a preferred embodiment of the absorbent article according to the present invention.

The disposable diaper 1 of the embodiment shown in FIG. 2 comprises a liquid permeable topsheet 2, a liquid impermeable back sheet 3 and an absorbent member (not shown) interposed between the topsheet and the backsheet, and has waist gathers 7 and 7' formed of the topsheet 2, the back sheet 3, and a first elastic member 6 sandwiched therebetween at the waist portion, i.e., a front waist portion 5 and a rear waist portion 5', respectively. The positions of the front waist portion 5 and the rear waist portion 5' correspond to the periphery of the front and rear ends of the absorbent member.

The leg openings, which are located at the longitudinal sides of the diaper 1 have leg gathers 9 and 9' formed of the topsheet 2, the back sheet 3, and a second elastic member 8 sandwiched therebetween.

Fastening tapes 10 and 10' are provided at both sides of the rear waist portion 5' of the diaper 1, with which the front waist portion 5 and the rear waist portion 5' are fastened together when the diaper 1 is put on a wearer. On the other hand, a landing tape 11 is provided on the surface of the back sheet 3 of the front waist portion 5, on which the fastening tapes 10 and 10' are to be stuck.

The absorbent member has a sandglass shape having a curved and narrowed portion corresponding to the crotch portion. The first elastic member 6 and the second elastic member 8 are provided in the expanded state between the topsheet 2 and the back sheet 3 at the periphery of the absorbent member, i.e., at the front waist portion 5, the rear waist portion 5', and the right and left leg openings. The first elastic member 6 and the second elastic member 8 contract in their free state to form the waist gathers 7 and 7' and the leg gathers 9 and 9' as shown in FIG. 2 so as to provide a good fit at the waist and the crotch of a wearer.

Materials forming the individual parts constituting the disposable diaper 1 will be explained below. The topsheet 2 is made of a liquid permeable sheet which transmits waste to the absorbent member and preferably feels like underwear. Such a liquid permeable sheet preferably includes woven fabric, nonwoven fabric, and perforated film. A sheet having its peripheral portion rendered water repellent so as to prevent leakage of urine, etc. due to oozing from the periphery can preferably be used. Treatment for rendering water repellent can be carried out by a method comprising coating the peripheral portion of the topsheet 2 with a hydrophobic compound, such as silicone oil or paraffin wax or a method comprising first coating the entire surface of the topsheet 2 with a hydrophilic compound, such as an alkyl phosphate and then washing the peripheral portion with warm water.

The absorbent member, which is interposed between the topsheet 2 and the back sheet 3, preferably includes the one made of a combination comprising comminuted pulp as main component and an absorbent polymer and the one made of a heat-treated mixture of a thermoplastic resin, cellulose fiber, and an absorbent polymer. A mixture of an absorbent polymer and pulp can also be used. In this case, the absorbent polymer may be present in any of the upper, middle and lower layers constituting the absorbent member. The absorbent polymer is preferably particles of polymers capable of absorbing and retaining 20 or more times as much liquid as its own weight and gelling upon liquid absorption. Suitable absorbent polymers include a starch-acrylic acid (or a salt thereof) graft copolymer, a saponified starch-acrylonitrile copolymer, crosslinked sodium carboxymethyl cellulose, and an acrylic acid (or a salt thereof) polymer.

The first elastic member 6 for the waist gathers 7 and 7' and the second elastic member 8 for the leg gathers 9 and 9' are preferably rubber of string, strip or film form, or films of polyurethane foam.

According to the embodiment shown in FIG. 2, the aforesaid composite sheet is used as the back sheet of the disposable diaper 1.

The composite sheet 20 is used with its nonwoven fabric 22 facing outward so that the disposable diaper 1 may have an improved texture or touch, such as improved softness, owing to the cloth-like texture of the nonwoven fabric 22. In addition, in case where the composite sheet 20 has a moisture permeable sheet as the sheet 21, high humidity inside the diaper and a resultant diaper rash can be prevented, since the water vapor can expire outside through the moisture permeable sheet.

While the composite sheet and the absorbent article of the present invention have been described with particular reference to their preferred embodiments, the present invention is not construed as being limited thereto, and various changes and modifications can be made therein.

For example, nonwoven fabric, which may be the same or different in kind from the nonwoven fabric 22, may be laminated on the side of the sheet 21 of the composite sheet according to the embodiment shown in FIG. 1 to have a three-layer structure.

In the composite sheet according to the embodiment shown in FIG. 1, the sheet 21 and the nonwoven fabric 22 may have either the same or different sizes. The nonwoven fabric 22 may be laminated on the sheet 21 either continuously or discontinuously.

The composite sheet is additionally applicable to various fields where a soft touch or texture and waterproofness, especially moisture permeability are demanded, such as waterproof clothes, waterproof covers, and wrapping materials.

While the embodiment shown in FIG. 2 is a flat-type disposable diaper, the absorbent article of the present invention can be applied to pants type disposable diapers. Further, the absorbent article of the present invention is not limited to disposable diapers and can be used as a sanitary napkin, a pad for incontinence, etc. as well.

Figure 3:
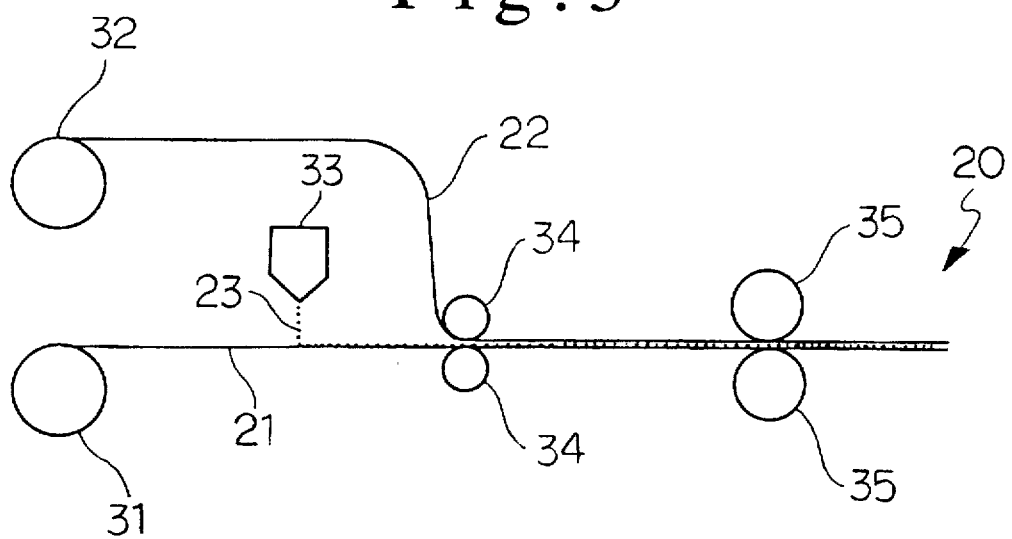
FIG. 3 is a schematic illustration of the apparatus used for carrying out a preferred process for producing the disposable diaper shown in FIG. 2.

A preferred process for producing the disposable diaper of the embodiment shown in FIG. 2 will now be illustrated by referring to the accompanying drawing. FIG. 3 is a schematic illustration of the apparatus used for carrying out in the preferred process for producing the disposable diaper shown in FIG. 2.

The composite sheet 20 as the back sheet 3 of the disposable diaper shown in FIG. 2 is preferably prepared by applying the aforesaid adhesive composition 23 having the above-specified physical properties on the aforesaid sheet 21 having the above-specified physical properties at the above-specified amount, laminating the above-described nonwoven fabric 22 having the above-specified physical properties to the sheet 21 via the adhesive composition 23, and securely joining the sheet 21 and the nonwoven fabric 22 to each other by heat embossing.

The terminology "heat embossing" as used herein means both embossing a preheated composite sheet and heat embossing by heated embossing means.

The above process will further be explained by referring to FIG. 3. The sheet 21 is unrolled from a roll 31 of the sheet, and the adhesive composition 23 is atomized and applied in a dot pattern to one side of the unrolled sheet 21 at the above-specified amount by means of a melt blown coater 33. Nonwoven fabric 22 unrolled from a roll 32 is laminated on the coated side of the sheet 21 to obtain the composite sheet, and the composite sheet is passed through a pair of nip rollers 34 to ensure the adhesion of the sheet 21 and the nonwoven fabric 22. Subsequently, the composite sheet is passed through a pair of embossing rollers 35,35 to conduct heat embossing. The thus obtained composite sheet 20 is wound up by means of a winder (not shown). In this case, the composite sheet may be passed through a pair of heat rollers instead of the embossing rollers 35,35 in order to enhance the adhesive strength.

The resulting composite sheet in a rolled form is unrolled in a conventional process of the manufacture of disposable diapers to produce the disposable diaper shown in FIG. 2.

The embossing rollers to be used are usually a combination of an engraved roller and a smoothing roller. The engraved roller can be, for example, an iron-made roller engraved with a pattern of various designs. The smoothing roller includes a paper roller, a rubber roller, a silicone rubber roller, a urethane rubber roller, and a metallic roller. In the apparatus shown in FIG. 3, either one or both of these embossing rollers is/are heated to conduct heat embossing.

The heating temperature of the embossing roller(s) is preferably lower than the melting point of the sheet 21 and/or nonwoven fabric 22 in direct contact with the heated roller(s) by at least 10° C. If the embossing roller is heated to a higher temperature, the composite sheet tends to stick to the heated roller or undergo shrinkage or wrinkling with heat.

Where both the engraved roller and the smoothing roller are heated, it is also preferable for the texture or softness of the resulting composite sheet to make a difference in temperature (e.g., a difference of 10° to 30° C.) between the two rollers. In this case, it is preferable that the engraved roller be heated to a higher temperature than the smoothing roller.

The pattern on the engraved roller is not limited and includes, for example, pins, dots, honeycomb cells, checks, vertical stripes, horizontal stripes, stitches, and decorative designs.

The linear pressure of the embossing rollers in the heat embossing is generally from 10 to 150 kg/cm, while depending on the thickness and running speed of the composite sheet to be embossed and the heating temperature of the embossing rollers.

As regards the other particulars of the process for producing the disposable diaper, techniques of conventional processes for the manufacture of disposable diapers are applied appropriately.

The advantages of the composite sheet and absorbent article of the present invention will be demonstrated in the following Examples, but it should be understood that the present invention is not deemed to be limited thereto. Unless otherwise indicated, all the parts are given by weight.

EXAMPLE 1

A hundred parts of linear low-density polyethylene (Ultzex 2520F produced by Mitsui Petrochemical Industries, Ltd.), 150 parts of surface-treated calcium carbonate (average particle size: 1 μm), and 10 parts of an ester whose composition and physical properties are shown in Table 1 below were kneaded in a twin-screw kneader and pelletized. The resulting pellets were fed to a blown-film extruder to obtain a sheet having a thickness of 40 μm. The resulting sheet was stretched at 50° C. to a stretch ratio of 2.3 by means of a rollerstretching machine to obtain a moisture-permeable microporous sheet having a thickness of 20 μm, a moisture permeability of 1.8 g/(100 cm$^2$.hr), and a basis weight of 20 g/m$^2$.

TABLE 1

| Ester Composition (Theoretical Molar Ratio in Charging) | SV (Saponification Value) | AV (Acid Value) | OHV (Hydroxyl Value) |
| --- | --- | --- | --- |
| S-40/TMP/AA = 4/2/1 | 240 | 1.5 | 9.9 |

S-40: Stearic acid (Lunac S-40, a trade name, a product of Koa Corp.)
TMP: Trimethylolpropane
AA: Adipic acid An adhesive composition having the composition shown in Table 2 below was applied in dots onto the resulting moisture-permeable sheet according to a melt blowing method by use of the apparatus shown in FIG. 3 under conditions of 190° C. in hot air temperature, 1.8 kg/cm$^2$ in blowing pressure, 1.0 g/m$^2$ in amount, 170° C. in coating temperature, and 200 m/min in coating speed.

On the coated surface was laminated suction heat bonded nonwoven fabric made of polyethylene staple fibers having a diameter of 1.5 deniers and having a basis weight of 22 g/m² and a thickness of 0.5 mm under a load of 0.5 g/cm², to obtain a composite sheet.

The resulting composite sheet was evaluated in terms of adhesive strength at a 25 mm width and an anti-blocking strength at a 50 mm width in accordance with the following test methods. The results obtained are shown in Table 3 below.

Further, disposable diapers shown in FIG. 2 were prepared by using the composite sheet. During the preparation, neither blocking of the composite sheet nor breakage of the composite sheet or clinging to the roller was observed. The resulting disposable diapers had good ventilation (breathability) and an improved texture or touch such as improved softness.

1) Measurement of Adhesive Strength

A 25 mm wide and 100 mm long strip was cut out of the composite sheet with its width direction agreeing with the MD direction of the composite sheet and its longitudinal direction agreeing with the CD direction. The strip specimen was subjected to a 180° peel test by means of a Tensilon tensile tester at a rate of pulling of 300 mm/min and at a measuring temperature of 20° C. to obtain an adhesive strength in the CD direction of the composite sheet.

2) Measurement of Anti-Blocking Strength

The composite sheet measuring about 1000 m was wound around a paper core, and the roll was stored at 50° C. for 1 week. After the roll was allowed to cool for a sufficient time, adjacent two layers of the composite sheet were cut out, as overlaid one on another, from the roll at the position 30 mm away from the surface of the paper core in the radial direction to prepare a double-layered specimen having a width of 50 mm in agreement with the CD direction of the composite sheet and a length of 100 mm in agreement with the MD direction. The specimen was subjected to a 180° peel test by means of a Tensilon tensile tester at a rate of pulling of 500 m/min and at a measuring temperature of 20° C. to obtain an anti-blocking strength.

EXAMPLES 2 TO 6

Composite sheets were prepared in the same manner as in Example 1, except for applying the adhesive composition under the conditions shown in Table 3 (Examples 2 to 6) and subjecting the composite sheet to heat embossing at the embossed area ratio shown in Table 3 (Examples 4 to 6). The heat embossing was carried out at an embossing roller temperature of 90° C. and a linear pressure of 60 kg/cm. The resulting composite sheets were evaluated in the same manner as in Example 1. The results obtained are shown in Table 3.

Disposable diapers shown in FIG. 2 were prepared using each of the composite sheets. During the preparation, neither blocking of the composite sheet nor breakage of the composite sheet or clinging to the roller was observed. The resulting disposable diapers had good ventilation (breathability) and an improved texture or touch such as improved softness.

COMPARATIVE EXAMPLE 1

A composite sheet was prepared in the same manner as in Example 1, except for replacing the adhesive composition used in Example 1 with a conventional SIS-based hot melt adhesive. The resulting composite sheet was evaluated in the same manner as in Example 1. The results obtained are shown in Table 3.

Disposable diapers shown in FIG. 2 were prepared by using the thus obtained composite sheet. During the preparation, breakage and clinging of the composite sheet to the roller due to blocking occurred.

TABLE 2

| | | |
|---|---|---|
| Base Polymer | APAO*¹ | 35 parts by wt. |
| Tackifier | Hydrogenated terpene resin*² | 60 parts by wt. |
| Softener | Paraffin oil*³ | 5 parts by wt. |
| Antioxidant | Hindered phenol*⁴ | 0.3 parts by wt. |
| Melt Viscosity at 180° C. (cps) | | 2000 |

Note:
*¹UT 2175, a product of Ube Rexene K.K.
*²CLEARON P105, a product of Yasuhara Kagaku K.K.
*³PW-90, a product of Idemitsu Kosan K.K.
*⁴Irganox 1010, a product of Ciba-Geigy Ltd.

TABLE 3

| | | Coating Temperature (°C.) | Hot Air Temperature/ Pressure (°C./kg/cm²) | Coating Speed (m/min.) | amount (g/m²) | Heat Embossing | Embossed Area Ratio (%) | Adhesive Strength (g/25 mm) | Blocking Strength (g/50 mm) |
|---|---|---|---|---|---|---|---|---|---|
| Examples | 1 | 170 | 190/1.8 | 200 | 1.0 | Not Conducted | — | 47 | ≦1 |
| | 2 | 170 | 190/1.8 | 200 | 1.5 | Not Conducted | — | 77 | 3 |
| | 3 | 170 | 190/1.8 | 200 | 2.0 | Not Conducted | — | 141 | 3 |
| | 4 | 170 | 190/1.8 | 200 | 1.0 | Conducted | 25 | 116 | ≦1 |
| | 5 | 170 | 190/1.8 | 200 | 1.5 | Conducted | 25 | 135 | 2 |
| | 6 | 170 | 190/1.8 | 200 | 2.0 | Conducted | 25 | 213 | 2 |
| Comparative Example | 1 | 170 | 190/1.8 | 200 | 1.0 | Not Conducted | — | 48 | 40 |

As is apparent from the results in Table 3, the composite sheets according to the present invention (Examples 1 to 6), which are obtained by laminating a sheet having specific physical properties and a nonwoven fabric having specific physical properties by an adhesive composition having specific physical properties, exhibit higher adhesive strength and yet lower anti-blocking strength, namely, anti-blocking properties, as compared with that obtained by using a conventional hot melt adhesive (Comparative Example 1).

In particular, the composite sheets obtained by subjecting a laminate of the moisture permeable sheet and the nonwoven fabric to heat embossing (Examples 4 to 6) exhibit extremely enhanced adhesive strength.

EXAMPLES 7 TO 12

A hundred parts of low density polyethylene (ULTZEX 2080 (trade name) produced by Mitsui Petrochemical Industries, Ltd.) and 5 parts of titanium oxide were kneaded in a twin-screw kneader and pelletized. The resulting pelltes were fed to a T-die extruder to obtain moisture impermeable sheets having a thickness of 20 μm. Composite sheets were prepared using the moisture impermeable sheets in the same manner as in Example 1, except for applying the adhesive composition of Example 1 under the conditions shown in Table 4 and subjecting the composite sheet to heat embossing at the embossed area ratio shown in Table 4 (Examples 10 to 12). The resulting composite sheets were evaluated in the same manner as in Example 1. The results obtained are shown in Table 4. The heat embossing was carried out in the same manner as in Examples 4 to 6.

Disposable diapers shown in FIG. 2 were prepared using each of the composite sheets. During the preparation, neither blocking of the composite sheet nor breakage of the composite sheet or clinging to the roller was observed.

TABLE 4

|  |  | Coating Temperature (°C.) | Hot Air Temperature/ Pressure (°C./kg/cm$^2$) | Coating Speed (m/min.) | amount (g/m$^2$) | Heat Embossing | Embossed Area Ratio (%) | Adhesive Strength (g/25 mm) | Blocking Strength (g/50 mm) |
| --- | --- | --- | --- | --- | --- | --- | --- | --- | --- |
| Examples | 7 | 170 | 190/1.8 | 200 | 1.0 | Not Conducted | — | 55 | ≦1 |
|  | 8 | 170 | 190/1.8 | 200 | 1.5 | Not Conducted | — | 90 | 4 |
|  | 9 | 170 | 190/1.8 | 200 | 2.0 | Not Conducted | — | 160 | 3 |
|  | 10 | 170 | 190/1.8 | 200 | 1.0 | Conducted | 25 | 120 | ≦1 |
|  | 11 | 170 | 190/1.8 | 200 | 1.5 | Conducted | 25 | 150 | 2 |
|  | 12 | 170 | 190/1.8 | 200 | 2.0 | Conducted | 25 | 220 | 2 |

As is apparent from the results in Table 4, the composite sheets according to the present invention (Examples 7 to 12), which are obtained by laminating a sheet having specific physical properties and a nonwoven fabric having specific physical properties by an adhesive composition having specific physical properties, exhibit high adhesive strength and yet low blocking strength, namely, anti-blocking properties.

In particular, the composite sheets obtained by subjecting a laminate of the moisture impermeable sheet and the nonwoven fabric to heat embossing (Examples 10 to 12) exhibit extremely enhanced adhesive strength.

What is claimed is:

1. A composite sheet comprising a liquid impermeable sheet and a nonwoven fabric joined to each other by an adhesive composition, said liquid impermeable sheet having a thickness of 15 to 40 μm; the nonwoven fabric having a fiber diameter of 1.5 to 3.5 deniers and a basis weight of 10 to 35 g/m$^2$; and the adhesive composition comprising not less than 20% by weight of an amorphous poly-α-olefin (APAO) having a melt viscosity of 500 to 10,000 cps at 180° C. and applied at an amount of 0.5 to 7 g/m$^2$.

2. The composite sheet according to claim 1, wherein the liquid impermeable sheet comprises a moisture permeable sheet having a moisture permeability of 0.5 to 4 g/(100 cm$^2$.hr).

3. The composite sheet according to claim 1, wherein the adhesive composition further comprises one or more of a tackifier, a softener or an antioxidant.

4. The composite sheet according to claim 1, wherein the adhesive composition has a melt viscosity of 1,000 to 8,000 cps at 180° C.

5. The composite sheet according to claim 1, which is heat embossed.

6. The composite sheet according to claim 5, wherein the composite sheet has an embossed area ratio of not more than 40% based on the total area of the composite sheet.

7. The composite sheet according to claim 1, wherein the adhesive strength between the sheet and the nonwoven fabric in the composite sheet is 30 g/25 mm or higher, and the composite sheet has an anti-blocking strength of 20 g/50 mm or less.

8. An absorbent article comprising a liquid permeable topsheet, a liquid impermeable back sheet and an absorbent member interposed between the topsheet and the back sheet, wherein the back sheet comprises the composite sheet according to claim 1.

9. A process for producing an absorbent article having a liquid impermeable back sheet which is a composite sheet comprising a liquid impermeable sheet and a nonwoven fabric joined to each other by an adhesive composition, said liquid impermeable sheet having a thickness of 15 to 40 μm; the nonwoven fabric having a fiber diameter of 1.5 to 3.5 deniers and a basis weight of 10 to 35 g/m$^2$; and the adhesive composition comprising not less than 20% by weight of an amorphous poly-α-olefin (APAO) having a melt viscosity of 500 to 10,000 cps at 180° C. and applied at an amount of 0.5 to 7 g/m$^2$, the process comprising the steps of applying the adhesive composition on the liquid impermeable sheet, laminating the nonwoven fabric to the liquid impermeable sheet via the adhesive composition, and securely joining the liquid impermeable sheet and the nonwoven fabric to each other by joining means.

10. A process for producing a composite sheet comprising a liquid impermeable sheet and a nonwoven fabric joined to each other by an adhesive composition, said liquid impermeable sheet having a thickness of 15 to 40 μm; the nonwoven fabric having a fiber diameter of 1.5 to 3.5 deniers and a basis weight of 10 to 35 g/m$^2$; and the adhesive composition comprising not less than 20% by weight of an amorphous poly-α-olefin (APAO) having a melt viscosity of 500 to 10,000 cps at 180° C. and applied at an amount of 0.5 to 7 g/m$^2$, the process comprising the steps of applying the adhesive composition on the liquid impermeable sheet, laminating the nonwoven fabric to the liquid impermeable sheet via the adhesive composition, and securely joining the liquid impermeable sheet and the nonwoven fabric to each other by joining means.

* * * * *